US00PP16823P2

(12) United States Plant Patent
Ui et al.

(10) Patent No.: US PP16,823 P2
(45) Date of Patent: Jul. 18, 2006

(54) ***CALIBRACHOA* PLANT NAMED 'KAKEGAWA S82'**

(50) Latin Name: ***Calibrachoa* sp.**
Varietal Denomination: Kakegawa S82

(75) Inventors: Akinobu Ui, Iwata (JP); Toshimi Ohga, Kikugawa (JP)

(73) Assignee: Sakata Seed Corporation, Yokohama (JP)

( * ) Notice: Subject to any disclaimer, the term of this patent is extended or adjusted under 35 U.S.C. 154(b) by 108 days.

(21) Appl. No.: 11/052,127

(22) Filed: Feb. 7, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Jondle & Associates P.C.

(57) ABSTRACT

'Kakegawa S82' is a new *Calibrachoa* cultivar particularly distinguished by having a scarlet-rose flower color and a creeping growth habit with a semi-erect center stem.

1 Drawing Sheet

Figure 1:
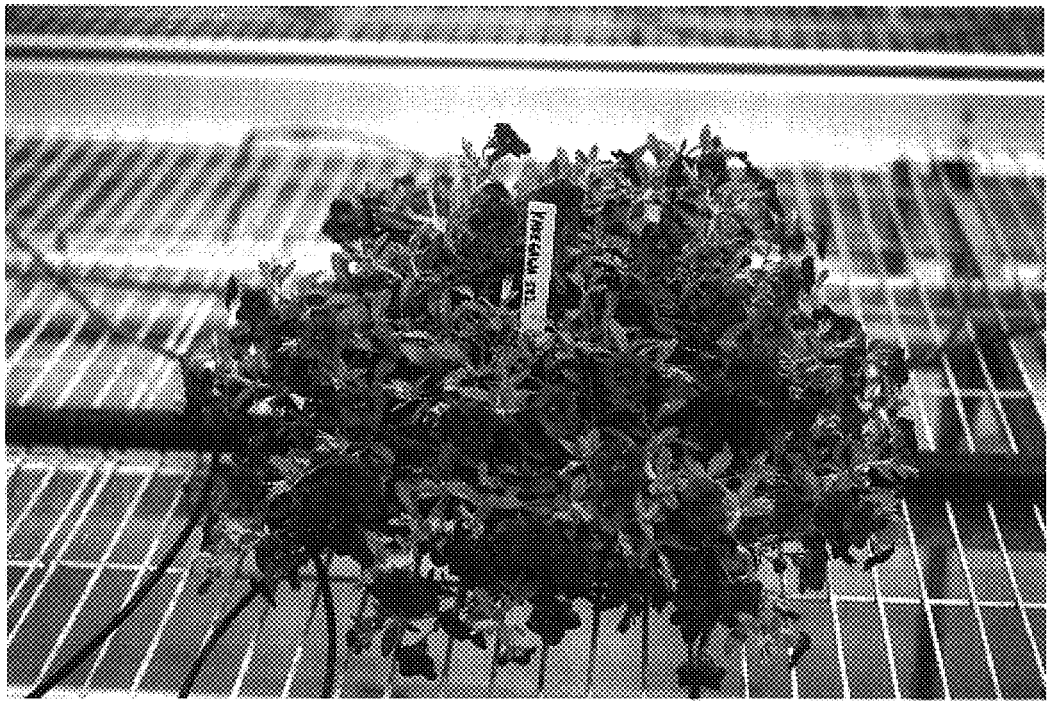

Genus and species: *Calibrachoa* sp.
Variety denomination: 'Kakegawa S82'.

BACKGROUND OF THE INVENTION

The present invention comprises a new and distinct cultivar of *Calibrachoa,* botanically known as *Calibrachoa* sp., and hereinafter referred to by the cultivar name 'Kakegawa S82'. It is characterized by having scarlet-rose flower color and creeping growth habit with a semi-erect center stem. The new cultivar originated from a hybridization made in Kakegawa, Japan in 1999. A proprietary *Calibrachoa* breeding line with a deep rose flower color and a creeping growth habit with an erect center stem (female) was crossed with *Calibrachoa* 'Kakegawa S24' (U.S. Plant Pat. No. 13,039) (male).

In August 1999, $F_1$ seed from the above hybridization was sown in the greenhouse. Four single-plant selections were made based on their creeping growth habit and intercrossed to produce $F_2$ seed. In February 2000, $F_2$ seed was sown and 100 total plants were evaluated. Four single-plant selections were made based on their creeping habit and intercrossed to produce $F_3$ seed. In August 2000, $F_3$ seed was planted and a total of 60 plants were evaluated. One single-plant selection was made based on its scarlet-rose flower color and creeping habit with a semi-erect center stem and asexually propagated through rooted plant cuttings in both Kakegawa, Japan and Salinas, Calif. 'Kakegawa S82' has been shown to reproduce true to type in successive generations of asexual propagation.

Description of the Genus *Calibrachoa* Llave & Lex

The genus *Petunia* was originally established in 1803 by A. L. Jussieu, who described both *P. parviflora* and *P. nyctaginiflora* as type species. Using a non-horticultural system that selected the first mentioned species as the type species (lectotype), N. L. Britton and H. A. Brown declared *P. parviflora* as the type species for *Petunia* in 1913.

During the 1980's and 1990, H. J. Wijsman published a series of articles regarding the ancestry of *P. hybrida,* the Garden *Petunia,* and the inter-relationship of several species classified as *Petunia.* These studies discovered that *P. hybrida* and its ancestral species, *P. nyctaginiflora* (=*P. axillaris*) and *P. violacea* (=*P. integrifolia*), possessed 14 pairs of chromosomes while several other species, including *P. parviflora,* possessed 18 pairs of chromosomes. Since *P. parviflora* was the lectotype species for the *Petunia* genus, Wijsman and J. H. de Jong proposed transferring the 14 chromosome species to the genus *Stimoryne.* Horticulturists opposed reclassifying the Garden *Petunia* and in 1986, Wijsman proposed the alternative of making *P. nyctaginiflora* the lectotype species for *Petunia* and transferring the 18 chromosome species to another genus. The I. N. G. Committee adopted this proposal. By 1990 Wijsman had transferred several species, including *P. parviflora* (=*C. parviflora*) to *Calibrachoa,* originally established by Llave and Lexarza in 1825. *Calibrachoa parviflora* (=*C. mexicana* Llave & Lexarza) is now the type species for the genus *Calibrachoa.*

Classification of the current *Petunia* and *Calibrachoa* species is still in progress. New species are also being identified. Consequently a proper description has not been written for the *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* bear a flower peduncle and three stems. *Petunia* species have a cochlear corolla bud, and a single outermost petal covers the other four, radially folded and terminally contorted petals. *Calibrachoa* flower buds are flat with all five petals linearly folded and the two lower petals forming a cover around the three other petals and fused together.

DESCRIPTION OF PHOTOGRAPHS

This new *Calibrachoa* plant is illustrated by the accompanying photographs which show the plant's form, foliage and flowers. The colors shown are as true as can be reasonably obtained by conventional photographic procedures.

FIG. 1. shows overall plant habit.

Figure 2:
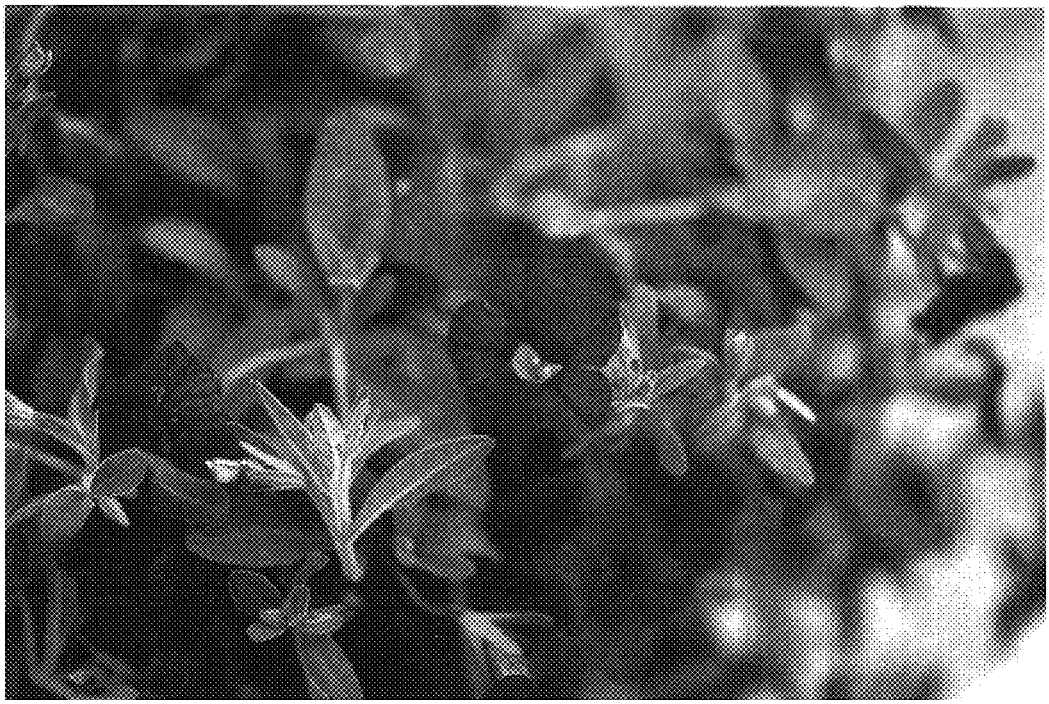

FIG. 2. shows the mature flower.

DESCRIPTION OF THE NEW CULTIVAR

The following detailed description sets forth the distinctive characteristics of 'Kakegawa S82'. The data which define these characteristics were collected from asexual reproductions carried out in Salinas, Calif. The detailed description was taken from plants grown under greenhouse conditions for approximately 4 months from transplanting of rooted cuttings. Color references are to The R.H.S. Colour Chart of The Royal Horticultural Society of London (R.H.S.), 4$^{th}$ Edition.

DETAILED BOTANICAL DESCRIPTION

Classification:
- *Family.*—Solanaceae.
- *Species.*—*Calibrachoa* sp. Cultivar 'Kakegawa S82'.
- *Common name.*—*Calibrachoa.*

Parentage:
- *Male.*—Unnamed and unknown proprietary breeding line.
- *Female.*—Unnamed and unknown proprietary *Calibrachoa* breeding line.

Plant description:
- *Life cycle.*—Tender Perennial.
- *Form.*—Branching.
- *Habit.*—Mounding.
- *Height.*—13 cm as measured from soil level to top of plant.
- *Spread.*—47 cm.

Propagation:
- *Type cuttings.*—Vegetative cuttings.
- *Time to produce a rooted cutting.*—5–6 weeks.
- *Time to bloom from propagation.*—10 weeks after root development.

Environmental conditions for plant growth: The terminal 1.0–1.5 inches of actively growing stems were excised and the base of each cutting dipped for one to two seconds in a 1:9 solution of DIP 'N GROW root inducing solution immediately prior to placing the cutting into a cell tray. The cell tray contained a moistened peat moss-based growing medium. The cuttings were misted with water from overhead for 10 seconds every 30 minutes until sufficient roots were formed. Rooted cuttings were transplanted and grown individually in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow-release fertilizer containing 20% nitrogen, 10% phosphorous and 18% potassium. The typical average air temperature was 24° C.

Stems:
- *Stem color.*—RHS 143C (green).
- *Anthocyanin color.*—RHS 79A (purple).
- *Pubescence.*—Heavy.
- *Pubescence color.*—RHS 155A (white).
- *Stem description.*—Ancipital (round).
- *Stem diameter.*—0.5 cm.
- *Stem length.*—2.5–3.0 cm.
- *Internode length.*—1.0 cm.

Leaves:
- *Leaf arrangement.*—Alternate.
- *Leaf shape.*—Elliptical.
- *Leaf apex.*—Mucronate.
- *Leaf base.*—Decurrent.
- *Leaf margin.*—Entire.
- *Leaf surface.*—Rough, dull.
- *Leaf surface pubescence.*—Slight.
- *Pubescence color.*—RHS 155A (white).
- *Venation.*—Pinnate.
- *Leaf length.*—2.5 cm.
- *Leaf width.*—0.8 cm.
- *Leaf color.*—Upper surface: RHS 139A (green). Lower surface: RHS 137C (green).
- *Petiole length.*—0.5 cm.
- *Petiole color.*—RHS 145A (yellow-green).

Inflorescence:
- *Flowering habit.*—Indeterminate.
- *Flower type.*—Solitary.
- *Flowering requirements.*—Will flower so long as day length is greater than 12 hours and temperature exceeds 13° C.
- *Duration of flowers.*—About 5 days.
- *Corolla shape.*—Flowers are funnel-shaped with five fused petals and five fissures dividing the petals and a shallow, yet prominent, indentation of the petal tip at the midvein.
- *Fragrance.*—Absent.

Flower buds:
- *Bud surface.*—Pubescent.
- *Bud length.*—1.5–1.7 cm.
- *Bud diameter.*—0.4 cm.
- *Bud shape.*—Ovate.
- *Bud color.*—RHS 160B (gray-yellow) with RHS 79A (purple) stripes.
- *Peduncle length.*—1.8–2.0 cm.
- *Peduncle color.*—RHS 144A (yellow-green).

Flower description:
- *Flower depth.*—2.0–2.2 cm.
- *Flower tube length.*—1.5 cm.
- *Flower tube diameter.*—0.5 cm.
- *Flower diameter.*—2.5 cm.
- *Calyx.*—5 sepals, free.
- *Sepals.*—Shape: Lanceolate. Apex: Mucronate. Margin: Entire. Sepal color: Upper surface: RHS 135A (green) at tip fading to RHS 143C (green) at base. Lower surface: RHS 141C (green).
- *Petal shape.*—Spatulate.
- *Petal length.*—1.0 cm.
- *Petal width.*—1.4 cm.
- *Petal apex.*—Mucronate.
- *Petal margin.*—Entire.
- *Petal texture.*—Glabrous.
- *Petal color.*—Lobe color: Upper surface: RHS 46A (red) with a RHS 79A (purple) midvein. Lower surface: RHS 182A (gray-red) with a RHS 79A (purple) midvein. Corolla tube color: Inner: RHS 14B (yellow-orange) with RHS 79A (purple) veins. Outer: RHS 160A (gray-yellow) with RHS 79A (purple) veins.

Reproductive organs:
- *Stamen number.*—5, free.
- *Stamen color.*—RHS 141 (green).
- *Pollen color.*—RHS 5A (yellow).
- *Ovary.*—Superior.
- *Pistil number.*—1 per inflorescence.
- *Pistil length.*—1.255 mm.
- *Stigma color.*—RHS 144A (yellow-green).
- *Style length.*—0.945 mm.
- *Style color.*—RHS 144A (yellow-green).

Disease and insect resistance: 'Kakegawa S82' has excellent resistance to rain, heat and drought, although it will not tolerate temperatures below 10° C. 'Kakegawa S82' is susceptible to *Botrytis,* powdery mildew, various stem and root rots, and certain viruses, such as Tobacco Mosaic Virus and *Impatiens* Necrotic Spotted Virus. 'Kakegawa S82' is also susceptible to aphids, leafminers, whiteflies and various *Lepidoptera.*

Comparison with Known Cultivars

*Calibrachoa* 'Kakegawa S82' is a distinct variety of *Calibrachoa* due to its scarlet-rose flower color and creeping growth habit with a semi-erect center stem. 'Kakegawa S82' is distinguished from known cultivars mainly by flower color as shown in Table 1 below.

TABLE 1

| Characteristic | 'Kakegawa S82' | Unnamed proprietary line | Unnamed proprietary line |
|---|---|---|---|
| Flower color | Scarlet rose with a purple midvein | Deep rose | White with pale yellow-green midveins |

'Kakegawa S82' is most similar to the variety 'Kakegawa S69' (U.S. Plant Pat. No. 15,524); however, there are differences in flower petal color and corolla tube color as described in Table 2 below.

TABLE 2

| Characteristic | 'Kakegawa S82' | 'Kakegawa S69' |
|---|---|---|
| Petal color, upper surface | RHS 46A (red) with RHS 79A (purple) midvein | RHS 40C (red) with RHS 46A (red) midvein |
| Petal color, lower surface | RHS 182A (gray-red) with RHS 79A (purple) midvein | RHS 31D (orange-red) with RHS 186B (gray-purple) midvein |
| Outer corolla tube color | RHS 160A (gray-yellow) with RHS 79A (purple) veins | RHS 10C (yellow) with RHS 186B (gray-purple) veins |

We claim:

1. A new and distinct cultivar of *Calibrachoa* plant as shown and described herein.

* * * * *